United States Patent [19]

Luengo et al.

[11] Patent Number: 5,981,551
[45] Date of Patent: Nov. 9, 1999

[54] 2,5-DIIMINO-3A,6A-DIARYL-1,2,3,3A,4,5,6,6A-OCTAHYDROIMIDAZO[4,5-D]IMIDAZOLES WHICH ARE EFFECTIVE AS G-CSF MIMETICS

[75] Inventors: Juan I. Luengo, Audubon; James A. Chan, West Chester; Ann L. Breen, Audubon, all of Pa.

[73] Assignee: SmithKline Beecham Corporation, Philadelphia, Pa.

[21] Appl. No.: 09/194,217

[22] PCT Filed: May 22, 1997

[86] PCT No.: PCT/US97/08864

§ 371 Date: Nov. 20, 1998

§ 102(e) Date: Nov. 20, 1998

[87] PCT Pub. No.: WO97/44033

PCT Pub. Date: Nov. 27, 1997

Related U.S. Application Data

[60] Provisional application No. 60/019,542, May 22, 1996.

[51] Int. Cl.$^6$ .................. A61K 31/415; A61K 31/44; C07D 235/00; C07D 401/14

[52] U.S. Cl. .................. 514/333; 514/338; 514/388; 546/256; 546/273.4; 548/303.4

[58] Field of Search ..................... 514/333, 338, 514/388; 546/256, 273.4; 548/303.4

[56] References Cited

U.S. PATENT DOCUMENTS 2,596,126 5/1952 Carhart et al. .................. 260/309

FOREIGN PATENT DOCUMENTS 49095992 9/1994 Japan .

OTHER PUBLICATIONS

Nishimura, et al., J. Org. Chem.; 1979, vol. 44, No. 5, pp. 818–824.
Furukawa, et al., Chem. Pharm. Bull.; 1974, vol. 21, No. 1, pp. 1–7.
Call, et al., Monatsh. Chem.; 1970, vol. 101, No. 2, pp. 344–356.

*Primary Examiner*—Laura L. Stockton
*Attorney, Agent, or Firm*—Wayne J. Dustman; William T. King; Charles M Kinzig

[57] ABSTRACT

Described herein are substituted 2,5-Diimino-3a,6a-diaryl-1,2,3,3a,4,5,6,6a-octahydroimidazo[4,5-d]imidazoles of formula (I), wherein $R^1$, $R^2$, $R^3$ and $R^4$ are defined therein, pharmaceutical compositions containing these compounds, methods of using these compounds as G-CSF Mimetics, and processes used in preparing these compounds.

(I)

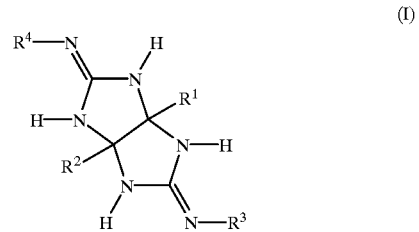

14 Claims, No Drawings

2,5-DIIMINO-3A,6A-DIARYL-1,2,3,3A,4,5,6,6A-OCTAHYDROIMIDAZO[4,5-D]IMIDAZOLES WHICH ARE EFFECTIVE AS G-CSF MIMETICS

This application is a 371 of International Application PCT/US97/08864, filed May 22, 1997, which claims benefit to U.S. Provisional Ser. No. 60/019,542, filed May 22, 1996.

BACKGROUND OF THE INVENTION

Granulocyte colony-stimulating factor (G-CSF) is a glycoprotein secreted by macrophages, fibroblasts, and endothelial cells originally identified by its ability to stimulate the survival, proliferation, and differentiation in vitro of predominantly neutrophilic granulocytes from bone marrow progenitors. Nicola, N. A., *Annu. Rev. Biochem.* (1989) 58:45. The capacity of G-CSF to regulate in vivo granulopoiesis is supported by animal and clinical studies, which demonstrated a reversible rise in circulating neutrophil levels in response to administered recombinant G-CSF. Gabrilove, J. L. et al., *N. Engl. J. Med.* (1988) 318:1414. G-CSF has pleiotropic effects on mature neutrophils, enhancing their survival and stimulating functional activation, including induction of neutrophil alkaline phosphatase (Sato. N. et al., *J. Cell. Physiol.* (1988) 37:272) and high affinity IgA $F_c$ receptors (Weisbart, R. H., et al., *Nature* (Lond.) (1988) 332:647), priming for respiratory burst (Nathan, C. F. *Blood* (1989) 73:301) and increased chemotaxis (Wang, J. M., *Blood* (1988) 72:1456). G-CSF effects have also been observed on hematopoietic cells that are not committed to the granulocyte lineage, for example, stimulation of the proliferation on monocytic differentiation in vitro of some myeloid leukemic cells (Geissler, K., *J. Immunol.* (1989) 143:140) and the proliferation in vitro of some multipotential hematopoietic precursors (Ferrero, D., *Blood* (1989) 73:402).

Administration of recombinant G-CSF to patients suffering from neutropenia due to various causes indicated that G-CSF is beneficial as an adjuvant in chemotherapy and in bone marrow transplantation (Morstyn, G., et al., *Trends Phannacol. Sci.* 10, (1989) 154–159). G-CSF activity is also associated with mobilization of hematopoietic stem cells from the marrow to the peripheral blood. (See review article, Good Review article Haylock et al., *Blood* 89:2233–2258, 1997).

It would be desirable to provide compounds which allow for the treatment of neutropenia to enhance leukocyte production by acting as a G-CSF mimetic.

As disclosed herein it has unexpectedly been discovered that certain non-peptide compounds are effective as G-CSF minmetics.

As disclosed herein it has unexpectedly been discovered that certain selected 2,5-Diimino-3a,6a-diaryl-1,2,3,3a,4,5,6,6a-octahydroimidazo[4,5-d]imidazoles are effective as G-CSF mimetics.

SUMMARY OF THE INVENTION

This invention relates to compounds of Formula (I):

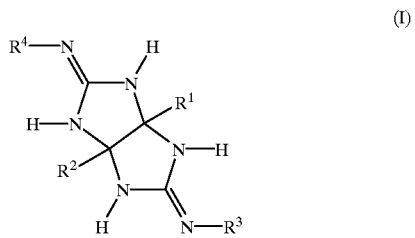

wherein $R^1$, $R^2$, $R^3$ and $R^4$ are independently aryl, where aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: C(O)NR$^6$R$^7$ and NR$^6$R$^7$, aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where
  $R^6$ is hydrogen or alkyl,
  n is 0–2,
  $R^7$ is hydrogen or alkyl and
  $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and pharmaceutically acceptable salts, hydrates, solvates and esters thereof.

The present invention also relates to the discovery that the compounds of Formula (I) are active as G-CSF mimetics.

The invention also is a method for treating neutropenia, including chemotherapy-induced neutropenia and bone marrow transplantation and in mobilizing peripheral blood stem cells and other conditions with depressed leukocyte production in mammals, including humans, which comprises administering to a subject in need thereof an effective amount of a presently invented G-CSF mimetic compound.

The invention is also a method for treating bacterial and fungal infections in mammals, including humans, which comprises administering to a subject in need thereof an effective amount of a presently invented G-CSF mimetic compound.

In a further aspect of the invention there is provided novel processes useful in preparing the presently invented G-CSF mimetic compounds.

Included in the present invention are pharmaceutical compositions comprising a pharmaceutical carrier and compounds useful in the methods of the invention.

Also included in the present invention are methods of co-administering the presently invented G-CSF mimetic compounds with further active ingredients.

This invention also relates to the discovery that certain non-peptide compounds are effective as G-CSF mimetics.

DETAILED DESCRIPTION OF THE INVENTION

The compounds of this invention that act as G-CSF mimetics have the following Formula (I):

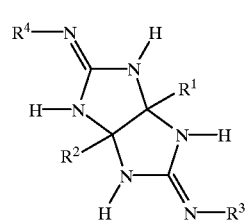

wherein $R^1, R^2, R^3$ and $R^4$ are independently aryl, where aryl is cyclic or polycyclic aromatic $C_3–C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: C(O)$NR^6R^7$ and $NR^6R^7$, aryloxy, cycloalkyl, substituted cycloalkyl, alkyl, $C_6–C_{12}$aryl, alkoxy, acyloxy, substituted $C_6–C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, $C_6–C_{12}$aryl, substituted $C_6–C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6–C_{12}$aryl, substituted cycloalkyl, substituted $C_6–C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6–C_{12}$aryl, substituted $C_6–C_{12}$aryl and protected —OH, where $R^6$ is hydrogen or alkyl, n is 0–2 and $R^7$ is hydrogen or alkyl; and pharmaceutically acceptable salts, hydrates, solvates and esters thereof.

Preferred among the presently invented Formula I compounds are those in which aryl is: $C_5–C_{12}$aryl, optionally containing one or two heteroatoms and optionally substituted with one or more substituents selected from the group consisting of: —OC$_6$–C$_{12}$ aryl, —(CH$_2$)$_m$OH, C$_6$–C$_{12}$ aryl, C$_1$–C$_4$ alkyl, —OC$_1$–C$_4$ alkyl, amino, nitro, cyano, N-acylamino, trifluoromethyl, C$_{3–7}$ cycloalkyl, halogen, —(CH$_2$)$_p$COOH, —S(O)$_n$R$^7$ and protected —OH, where m is 0–4, p is 0–3, n is 0–2 and $R^7$ is hydrogen or C$_{1–4}$alkyl; and pharmaceutically acceptable salts, hydrates, solvates and esters thereof.

Particularly preferred among the presently invented compounds are those in which $R^1$ and $R^2$ are independently phenyl, naphthyl, furyl, thienyl, pyridyl, indolyl or quinolyl all of which are unsubstituted or substituted with a substituent selected from the group consisting of: halogen, C$_{1–5}$ alkyl, C$_{3–7}$ cycloalkyl and —O—C$_{1–4}$ alkyl; $R^3$ and $R^4$ are independently phenyl, naphthyl, thienyl, pyridyl, quinolyl, benzimidazolyl benzothiazolyl, benzoxazolyl, thiazolyl or imidazolyl all of which are unsubstituted or substituted with one or two substituents selected from the group consisting of: halogen, amino, cyano, N-acylamino, C$_{1–3}$ alkyl, —O—C$_{1–3}$ alkyl, nitro, —CO$_2$H and CF$_3$; and pharmaceutically acceptable salts, hydrates, solvates and esters thereof.

Particularly preferred among the presently invented compounds are those in which $R^1$ and $R^2$ are independently phenyl, furyl, thienyl or pyridyl all of which are unsubstituted or substituted with a substituent selected from the group consisting of: halogen, C$_{1–5}$ alkyl, C$_{3–6}$ cycloalkyl and —O—C$_{1–3}$ alkyl;

$R^3$ and $R^4$ are independently pyridyl, benzimidazolyl, benzothiazolyl, benzoxazolyl, thiazolyl or imidazolyl all of which are unsubstituted or substituted with one or two substituents selected from the group consisting of: halogen, amino, cyano, N-acylamino, C$_{1–3}$ alkyl, —O—C$_{1–3}$ alkyl, nitro, —CO$_2$H and CF$_3$; and pharmaceutically acceptable salts, hydrates, solvates and esters thereof.

The most preferred compounds of the present invention are those in which $R^1$ and $R^2$ are 2-pyridyl both of which are independently unsubstituted or substituted with C$_{1–3}$alkyl; and $R^3$ and $R^4$ are 2-benzimidazolyl both of which are independently unsubstituted or substituted with C$_{1–3}$alkyl, provided that $R^3$ and $R^4$ are not both substituted.

Preferred among the presently invented compounds are:

2,5-bis[2-benzimidazolylimino]-3a,6a-bis(2-pyridyl)-1,2,3,3a,4,5,6,6a-octahydroimidazo[4,5-d]imidazole, 2,5-bis[2-benzimidazolylimino]-3a-(2-pyridyl)-6a-phenyl-1,2,3,3a,4,5,6,6a-octahydroimidazo[4,5-d]imidazole, 5-[2-benzimidazolylimino]-2-[(4-methyl-2-benzimidazolyl)imino]-3a,6a-bis(2-pyridyl)-1,2,2a,4,5,6,6a-octahydroimidazo[4,5-d]imidazole bis(trifluoroacetate) salt, 5-[2-benzimidazolylimino]-2-[(5-methyl-2-benzimidazolyl)imino]-3a,6a-bis(2-pyridyl)-1,2,3,3a,4,5,6,6a-octahydroimidazo[4,5-d]imidazole bis(trifluoroacetate) salt, 2,5-bis[(1-methyl-2-benzimidazolyl)imino]-3a,6a-bis(2-pyridyl)-1,2,3,3a,4,5,6,6a-octahydromidazo[4,5-d]imidazole bis(trifluoroacetate) salt, 5-[2-benzimidazolylimino]-2-[(5,6-dimethyl-2-benzimidazolyl)imino]-3a,6a-bis(2-pyridyl)-1,2,2a,4,5,6,6a-octahydroimidazo[4,5-d]imidazole bis(trifluoroacetate) salt, 2,5-bis[2-benzimidazolylimino]-3a,6a-diphenyl-1,2,3,3a,4,5,6,6a-octahydroimidazo[4,5-d]imidazole, 2,5-bis[2-benzimidazolylimino]-3a,6a-bis(2-furyl)-1,2,3,3a,4,5,6,6a-bis(2-pyridyl)octahydroimidazo[4,5-d]imidazole, 2,5-bis[2-benzimidazolylimino]-3a,6a-bis(3-methoxyphenyl)-1,2,3,3a,4,5,6,6a-octahydroimidazo[4,5-d]imidazole, 2,5-bis[2-benzimidazolylimino]-3a,6a-bis(4-methylphenyl)-1,2,3,3a,4,5,6,6a-octahydroimidazo[4,5-d]imidazole, 2,5-bis[2-benzimidazolylimino]-3a,6a-bis(4-fluorophenyl)-1,2,3,3a,4,5,6,6a-octahydroimidazo[4,5-d]imidazole, 2,5-bis[2-benzimidazolylimino]-3a,6a-bis(6-methyl-2-pyridyl)-1,2,3,3a,4,5,6,6a-octahydroimidazo[4,5-d]imidazole, 2,5-bis[2-benzimidazolylimino]-3a-(4-pyridyl)-6a-phenyl-1,2,3,3a,4,5,6,6a-octahydroimidazo[4,5-d]imidazole, 2,5-bis[(5-methyl-2-benzimidazolyl)imino]-3a,6a-bis(2-pyridyl)-1,2,3,3a,4,5,6,6a-octahydroimidazo[4,5-d]imidazole, 2,5-bis[(5-nitro-2-benzimidazolyl)imino]-3a,6a-bis(2-pyridyl)-1,2,3,3a,4,5,6,6a-octahydroimidazo[4,5-d]imidazole, 2,5-bis[(5-chloro-2-benzimidazolyl)imino]-3a,6a-bis(2-pyridyl)-1,2,3,3a,4,5,6,6a-octahydroimidazo[4,5-d]imidazole, 2,5-bis[(4-methyl-2-thiazolyl)imino]-3a,6a-bis(2-pyridyl)-1,2,3,3a,4,5,6a-octahydroimidazo[4,5-d]imidazole, 2,5-bis[2-benzoxazolylimino]-3a,6a-bis(2-pyridyl)-1,2,3a,4,5,6,6a-octahydroimidazo[4,5-d]imidazole, 2,5-bis[(4-methyl-2-benzimidazolyl)imino]-3a,6a-bis(2-pyridyl)-1,2,2a,4,5,6,6a-octahydroimidazo[4,5-d]imidazole, 5-(2-benzimidazolylimino)-2-[(5-fluoro-2-benzimidazolyl)imino]-3a,6a-bis(2-pyridyl)-1,2,3,3a,4,5,6,6a-octahydroimidazo[4,5-d]imidazole bis(trifluoroacetate) salt, 2,5-bis[(5-fluoro-2-benzimidazolyl)imino]-3a,6a-bis(2-pyridyl)-1,2,3,3a,4,5,6,6a-octahydroimidazo[4,5-d]imidazole bis(trifluoroacetate) salt, 5-(2-benzimidazolylimino)-2-[(1-methyl-2-benzimidazolyl)imino-3a,6a-bis(2-pyridyl)-1,2,3,3a,4,5,6,6a-octahydroimidazo[4,5-dlimidazole bis(trifluoroacetate) salt, 5-[2-benzimidazolylimino]-2-[(4-methyl-2-thiazolyl)imino)-3a,6a-bis(2-pyridyl)-1,2,2a,4,5,6,6a-octahydroimidazo[4,5-d]imidazole bis(trifluoroacetate) salt, 2,5-bis[(5-bromo-4-methyl-2-thiazolyl)imino]-3a,6a-bis(2-pyridyl)-1,2,3,3a,4,5,6a-octahydroimidazo[4,5-d]imidazole, 5-[2-benzimidazolylimino]-2-[(5-chloro-2-benzimidazolyl)imino]-3a,6a-bis(2-pyridyl)-1,2,2a,4,5,6,6a-octahydroimidazo[4,5-dlimidazole bis(trifluoroacetate) salt, 2,5-bis[(5,6-dimethyl-2-benzimidazolyl)imino]-3a,6a-bis(2-pyridyl)-1,2,2a,4,5,6,6a-octahydroimidazo[4,5-d]imidazole bis(trifluoroacetate) salt, 2,5-bis[(5-carboxy-2-benzimidazolyl)imino]-3a,6a-bis(2-pyridyl)-1,2,2a,4,5,6,6a-octahydroimidazo[4,5-d]imidazole bis(trifluoroacetate) salt, 5-[2-benzimidazolylimino]-2-[2-benzoxazolylimino-3a,6a-bis(2-pyridyl)-1,2,3a,4,5,6,6a-octahydroimidazo[4,5-d]imidazole bis(trifluoroacetate) salt, 2,5-bis[2-benzothiazolylimino]-3a,6a-bis(2-pyridyl)-1,2,3a,4,5,6,6a-octahydroimidazo[4,5-d]imidazole, 5-[2-benzimidazolylimino]-2-[2-benzothiazolylimino]-3a,6a-bis(2-pyridyl)-1,2,3a,4,5,6,6a-octahydroimidazo[4,5-d]imidazole bis(trifluoroacetate) salt, 5-[(2-benzimidazolylimino)]-2-[(5-carboxy-2-benzimidazolyl)imino]-3a,6a-bis(2-pyridyl)-1,2,3,3a,4,5,6,6a-octahydroimidazo[4,5-d]imidazole bis(trifluoroacetate) salt, 2,5-bis[(5-iodo-2-benzimidazolyl)imino]-3a,6a-bis(2-pyridyl)-1,2,3,3a,4,5,6,6a-octahydroimidazo[-4,5-d]imidazole bis(trifluoroacetate) salt, and 5-[2-benzimidazolylimino]-2-[(5-iodo-2-benzimidazolyl)imino]-3a,6a-bis(2-pyridyl)-1,2,2a,4,5,6,6]a-octahydroimidazo[4,5-d]imidazole bis(trifluoroacetate) salt.

2,5-bis[2-benzimidazolylimino]-3a,6a-bis(4-bromophenyl)-1,2,3,3a,4,5,6,6a-octahydroimidazo[4,5-d]imidazole, 2,5-bis[2-benzimidazolylimino]-3a,6a-bis(4-trifluoromethylphenyl)-5 1,2,3,3a,4,5,6,6a-octahydroimidazo[4,5-dlimidazole, 1,2,3,3a,4,5,6,6a-octahydroimidazo[4,5-d]imidazole, 2,5-bis[2-benzimidazolylimino]-3a-(2-chlorophenyl)-6a-phenyl-1,2,3,3a,4,5,6,6a-octahydroimidazo[4,5-d]imidazole, 5-(2-benzimidazolylimino)-2-[(5-methyl-2-benzimidazolylimino)-6a-phenyl-3a-(2-pyridyl)-1,2,3,3a,4,5,6,6a-octahydroimidazo[4,5-d]imidazole bis(trifluoroacetate) salt, 2,5-bis[(1-methyl-2-benzimidazolyl)imino]-3a,6a-diphenyl-1,2,3,3a,4,5,6,6a-octahydromidazo[4,5-d]imidazole, 2,5-bis[(1-methyl-2-benzimidazolyl)imino]-3a,6a-bis(4-methylphenyl)-1,2,3,3a,4,5,6,6a-octahydromidazo[4,5-d]imidazole, and 2,5-bis[(1-methyl-2-benzimidazolyl)imino]-3a,6a-bis(4-bromophenyl)-1,2,3,3a,4,5,6,6a-octahydromidazo[4,5-d]imidazole.

By the term "protected hydroxy" or "protected —OH" as used herein, is meant the alcoholic or carboxylic—OH groups which can be protected by conventional blocking groups in the art as described in "Protective Groups In Organic Synthesis" by Theodora W. Greene, Wiley-Interscience, 1981, New York.

By the term "$C_5$–$C_{12}$ aryl" as used herein, unless otherwise defined, is meant a cyclic or polycyclic aromatic $C_5$–$C_{12}$ optionally containing one or two heteroatoms.

By the term "$C_6$–$C_{12}$ aryl" as used herein, unless otherwise defined, is meant phenyl, naphthyl, 3,4-methylenedioxyphenyl, pyridyl, or biphenyl.

By the term "substituted" as used herein, unless otherwise defined, is meant that the subject chemical moiety has one or more substituents selected from the group consisting of: hydroxyalkyl, alkoxy, acyloxy, alkyl, amino, N-acylamino, hydroxy, —$(CH_2)_gC(O)OR^6$, —$S(O)_nR^7$, nitro, cyano, halogen, trifluoromethyl and protected —OH, where g is 0–6, $R^6$ is hydrogen or alkyl, n is 0–2, and $R^7$ is hydrogen or alkyl.

By the term "alkoxy" as used herein is meant —OC(O) alkyl where alkyl is as described herein including —$OCH_3$ and —$OC(CH_3)_2CH_3$.

The term "cycloalkyl" as used herein unless otherwise defined, is meant a nonaromatic, unsaturated or saturated, cyclic or polycyclic $C_3$–$C_{12}$ Examples of cycloalkyl and substituted cycloalkyl substituents as used herein include: cyclohexyl, 4hydroxy-cyclohexyl, 2-ethylcyclohexyl, propyl 4-methoxycyclohexyl, 4-methoxycyclohexyl, 4-carboxycyclohexyl and cyclopentyl.

By the term "acyloxy" as used herein is meant —OC(O) alkyl where alkyl is as described herein. Examples of acyloxy substituents as used herein include: —$OC(O)CH_3$, —$OC(O)CH(CH_3)_2$ and —$OC(O)(CH_2)_3CH_3$.

By the term "N-acylamino" as used herein is meant —N(H)C(O)alkyl, where alkyl is as described herein. Examples of N-acylamino substituents as used herein include: —$N(H)C(O)CH_3$, —$N(H)C(O)CH(CH_3)_2$ and —$N(H)C(O)(CH_2)_3CH_3$.

By the term "aryloxy" as used herein is meant —$OC_6$–$C_{12}$aryl where $C_6$–$C_{12}$aryl is phenyl, naphthyl, 3,4-methylenedioxyphenyl, pyridyl or biphenyl optionally substituted with one or more substituents selected from the group consisting of: alkyl, hydroxyalkyl, alkoxy, trifuloromethyl, acyloxy, amino, N-acylamino, hydroxy, —$(CH_2)_gC(O)OR^6$, $S(O)_nR^7$, nitro, cyano, halogen and protected —OH, where g is 0–6, $R^6$ is hydrogen or alky, n is 0–2 and $R^7$ is hydrogen or alkyl. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain having $C_1$—$C_{12}$ carbon atoms. Examples of alkyl substituents as used herein include: —$CH_3$, —$CH_2$–$CH_3$, —$CH_2$–$CH_2$–$CH_3$, —CH($CH_3$)$_2$, —C($CH_3$)$_3$, —($CH_2$)$_3$–$CH_3$, —$CH_2$–CH($CH_3$)$_2$ and —CH($CH_3$)—$CH_2$–$CH_3$, —CH═$CH_2$.

By the term "treating" and derivatives thereof as used herein, is meant prophylatic or therapeutic therapy.

By the phrase "mobilizing peripheral blood stem cells" as used herein is meant the mobilization of hematopoietic stem cells from the marrow to the peripheral blood.

By the phrase "non-peptide bifunctional ligand" as used herein is meant a ligand capable of activating the G-CSF receptor by binding to two non-adjacent sites.

By the phrase "non-peptide" as used herein is meant protein or peptide not comprising primarily of natural amino acids.

By the term "primarily" as used herein, unless otherwise defined, is meant less than 60% by weight of the naturally occurring amino acid residue.

All publications, including but not limited to patents and patent applications, cited in this specification are herein incorporated by reference as if each individual publication were specifically and individually indicated to be incorporated by reference herein as though fully set forth.

Compounds of Formula (I) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics for use as sustained release or prodrug formulations.

By the term "co-administering" and derivatives thereof as used herein is meant either simultaneous administration or any manner of separate sequential administration of a G-CSF mimetic compound, as described herein, and a further active ingredient or ingredients, such as antibacterial agents, antifungal agents as well as agents known to treat neutropenia, including chemotherapy-induced neutropenia and bone marrow transplantation and in mobilizing peripheral blood stem cells and other conditions with depressed leukocyte production. Preferably, if the administration is not simultaneous, the compounds are administered in a close time proximity to each other. Furthermore, it does not matter if the compounds are administered in the same dosage form, e.g. one compound may be administered topically and another compounds may be administered orally.

The novel compounds of Formula (I) are prepared as shown in Scheme I below provided that the 'R' substituents do not include any such substituents that render inoperative the Scheme I process. The 1,2-Diketones of Formula (2) are commercially available or prepared from aryl aldehydes by benzoin condensation according to the procedure described in Ide et al (Organic Reactions vol IV, 269) followed by oxidation of intermediate alpha-hydroxy ketones as reported by Mancuso et al. (J. Org. Chem. 1979, 44, 4148). The guanidine derivatives of Formula (3) are commercially available or can be readily prepared from commercially available o-phenylenediamines following the procedure of King et al (J. Chem. Soc. 1948,1366).

Scheme (I)
Preparation of Compounds of Formula (I)
Compounds of Formula (I)

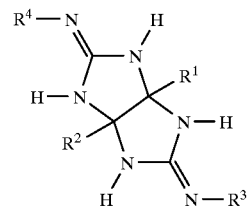

(I)

wherein $R^1$, $R^2$, $R^3$ and $R^4$ are as described in Formula (I) above; are prepared by treating a 1,2-diketone of Formula (2)

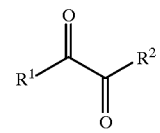

(2)

wherein $R^1$ and $R^2$ are as described in Formula (I) with one or more guanidine derivatives of Formula (3)

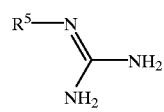

(3)

wherein $R^5$ is $R^3$ or $R^4$, such that when more than one guanidine derivative of Formula (3) is utilized, $R^5$ is not the same substituent. The reaction is run in a solvent such as benzene or pyridine at reflux with azeotropic removal of water such as by using a Dean-Stark apparatus or, alternatively, in the presence of a base catalyst (such as sodium hydroxide) in a suitable protic solvent (such as methanol, ethanol or water).

Pharmaceutically acceptable salts, hydrates and solvates are formed when appropriate by methods well known to those of skill in the art.

Because the pharmaceutically active compounds of the present invention are active as G-CSF mimetics they exhibit therapeutic utility in treating bacterial infections, fungal infections, neutropenia, including chemotherapy-induced neutropenia and bone marrow transplantation and in mobilizing peripheral blood stem cells and other conditions with depressed leukocyte production.

In determining potency as G-CSF mimetics, the following assays were employed:
Luciferase Assay Compounds of the present invention were tested for potency as mimetics of the G-CSF receptor in a Luciferase assay such as described in Lamb, et al., *Nucleic Acids Research* 23: 3283–3289 (1995) and Seidel, et al., *Proc. Natl. Acad. Sci.*, USA 92: 3041–3045 (1995) by substituting NFS60 cells for the HepG2 cells utilized therein. The NFS60 cells (Holmes, et al., *Proc. Natl. Acad. Sci.* USA 82: 6687–6691 (1985)) were substituted for the HepG2 cells in the Lamb assay because the NSF60 cells express endogenous G-CSF receptors closely matching the pattern of STAT (signal transducers and activators of transcription) activation observed in primary murine and human bone marrow cells.

Some of the most preferred compounds of this invention were also active in a CFU-G assay, an example of which is described in King A G, Talmadge J., Badger A M, Pelus L M. Regulation of colony stimulating activity production from bone marrow stromal cells by the hematoregulatory peptide, HP-5. *Exp. Hematol.* 20:223–228, 1992.

The pharmaceutically active compounds within the scope of this invention are useful as G-CSF mimetics in mammals, including humans, in need thereof.

The compounds of Examples 1, 2, 4–8, 13, 15–18, 20, 25, 26, 30, 32b, 34, 35, 37 and 39 showed activation above 150% of control between the concentration range of 1 to 32 uM in the luciferase assay.

The compounds of Examples 3, 9–12, 14, 19, 21–24, 27–29, 31, 32a, 33, 36, 38 and 40, although not showing an activation above 150% of control between the concentration range of 1 to 32 uM, were believed to show activation of above 150% of control at >32 uM in the luciferase assay.

The present invention therefor provides a method of treating bacterial infections, fungal infections, neutropenia, including chemotherapy-induced neutropenia and bone marrow transplantation and in mobilizing peripheral blood stem cells and other conditions with depressed leukocyte production, which comprises administering a compound of Formula (I):

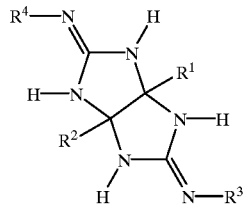

(I)

wherein $R^1$, $R^2$, $R^3$ and $R^4$ are independently aryl, where aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: C(O)NR$^6$R$^7$ and NR$^6$R$^7$, aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where R$^6$ is hydrogen or alkyl, n is 0–2 and R$^7$ is hydrogen or alkyl; and pharmaceutically acceptable salts, hydrates, solvates and esters thereof in a quantity effective to enhance leukocyte production. The compounds of Formula (I) also provide for a method of treating the above indicated disease states because of their demonstrated ability to act as G-CSF minmetics. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001–100 mg/kg of active compound, preferably 0.001–50 mg/kg. When treating a human patient in need of a G-CSF mimetic, the selected dose is administered preferably from 1–6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular G-CSF mimetic in use, the strength of the preparation, the mode of administration, and the advancement of the disease condition. Additional factors depending on the particular patient being treated will result in a need to adjust dosages, including patient age, weight, diet, and time of administration.

The method of this invention of inducing G-CSF mimetic activity in mammals, including humans, comprises administering to a subject in need of such activity an effective G-CSF mimetic amount of a pharmaceutically active compound of the present invention.

The invention also provides for the use of a compound of Formula (I) in the manufacture of a medicament for use as a G-CSF mimetic.

The invention also provides for the use of a compound of Formula (I) in the manufacture of a medicament for use in therapy.

The invention also provides for the use of a compound of Formula (I) in the manufacture of a medicament for use in enhancing leukocyte production.

The invention also provides for the use of a compound of Formula (I) in the manufacture of a medicament for use in treating bacterial and fungal infections.

The invention also provides for a pharmaceutical composition for use as a G-CSF mimetic which comprises a compound of Formula I and a pharmaceutically acceptable carrier.

The invention also provides for a pharmaceutical composition for use in the treatment of neutropenia which comprises a compound of Formula I and a pharmaceutically acceptable carrier.

The invention also provides for a pharmaceutical composition for use in enhancing leukocyte production which comprises a compound of Formula I and a pharmaceutically acceptable carrier.

The invention also provides for a pharmaceutical composition for use in treating bacterial infections which comprises a compound of Formula I and a pharmaceutically acceptable carrier.

The invention also provides for a pharmaceutical composition for use in treating fungal infections which comprises a compound of Formula I and a pharmaceutically acceptable carrier.

The invention also provides for a process for preparing a pharmaceutical composition containing a pharmaceutically acceptable carrier or diluent and a compound of Formula I which comprises bringing the compound of Formula I into association with the pharmaceutically acceptable carrier or diluent.

No unacceptable toxicological effects are expected when compounds of the invention are administered in accordance with the present invention.

In addition, the pharmaceutically active compounds of the present invention can be co-administered with further active ingredients, such as other compounds known to treat bacterial infections, fungal infections, neutropenia, including chemotherapy-induced neutropenia and bone marrow transplantation and in mobilizing peripheral blood stem cells and other conditions with depressed leukocyte production, or compounds known to have utility when used in combination with a G-CSF mimetic.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

EXAMPLE 1

Preparation of 2,5-bis[2-benzimidazolylimino]-3a, 6a-bis(2-pyridl)-1,2,3,3a,4,5,6,6a-octahydroimidazo[4,5-d]imidazole (Compound 1)

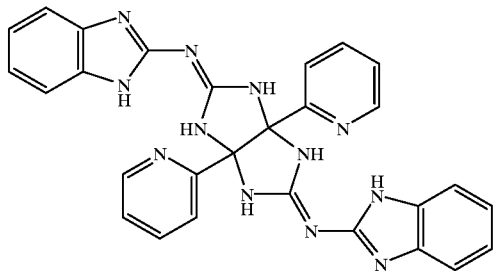

A mixture of 2,2'-pyridil (15.8 g, 74.4 mmol) and 2-guanidinobenzimidazole (19.5 g, 111.7 mmol) in methanol (440 mL) was treated with a solution of sodium hydroxide (2.97 g, 74.4 mmol) in 74 mL and the resulting mixture was left standing at room temperature for 4 days. The crystalline material was filtered and dried under vacuum to yield 21.1 g of the title compound as off-white crystals (72%). mp: 305–307° C. (dec); $^1$H NMR (300 MHz, $d_6$-DMSO) δ 11.5 (br s, NH, 2 H), 10.0 (br s, NH,2H),8.6 (brs,NH,2H),8.38(d,J=4.2 Hz,2H),7.55 (t,J=7.8 Hz,2H), 7.29 (d, J=7.8 Hz, 2 H), 7.27–7.21 (m, 4 H), 7.14 (br s, 2 H), 6.98 (dd, J=5.8,3.2 Hz, 4 H); MS (ESI) m/z 527 [M+H]$^+$; Anal. Calcd. for $C_{28}H_{22}N_{12}$. 2/3$H_2O$: C, 62.44; H, 4.37. N, 31.21; Found: C, 62.72; H, 4.08; N, 30.86.

EXAMPLE 2

Preparation of 2,5-Bis]2-benzimidazolylimino]-3a, 6a-diphenyl-1,2,3,3a,4,5,6,6a-octahydroimidazo]4,5-d]imidazole (Compound 2)

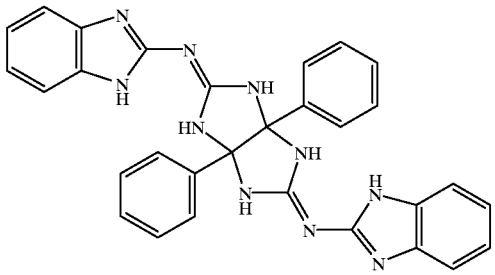

A mixture of benzil (1.05 g, 5.0 mmol) and 2-guanidinobenzimidazole (1.57 g, 9.0 mmol) in benzene (25 mL) was refluxed in pyridine (10 mL) for 1 h. After evaporating most of the pyridine under reduced pressure, the residue was treated with hot toluene and the resulting precipitate was filtered. The precipitate was then dissolved in 9:1 water:acetic acid (30 mL); the solution was filtered and the filtrate was neutralized to pH 7 with phosphate buffer. A precipitate formed, that was then collected and triturated with water to afford the title compound (0.42 g, 16%). $^1$H NMR (300 MHz, $d_6$-DMSO) δ 11.5 (br s, NH, 2 H), 10.0 (br s, NH, 2 H), 8.6 (br s, NH, 2 H), 7.28–7.10 (m, 14 H), 6.97 (dd, J=6.0, 3.0 Hz, 4 H); MS (ESI) m/z 525 [M+H]$^+$; Anal. Calcd. for $C_{30}H_{24}N_{10}$. 1/2 $CH_3CO_2H$. 3/4$H_2O$: C, 65.37; H, 4.88; N, 24.65. Found: C, 65.36; H, 4.79; N, 24.48.

EXAMPLE 3

Preparation of 2,5-bis[2-benzimidazolylimino]-3a, 6a-bis(2-furyl)-1,2,3,3a,4,5,6,6a-bis(2-pyridyl) octahydroimidazo[4.5-d]imidazole Following the procedure of Example 1, 2,2'-furil (1.91 g, 10 mmol) and 2-guanidinobenzimidazole (2.10 g, 12.0 mmol) in methanol (60 mL) was treated with a solution of sodium hydroxide (400 mg, 10 mmol) in 10 mL of water. The black precipitate was filtered, dissolved 30 mL of 10% acetic acid and filtered. The filtrate was neutralized with aqueous sodium hydroxide. The title compound precipitated as a grey solid (105 mg, 10% yield). mp: 222–225 ° C. (dec); MS (ESI) m/z 505 [M+H]$^+$.

EXAMPLE 4

Preparation of 2,5-bis[2-benzimidazolylimino]-3a, 6a-bis(3-methoxyphenyl)-1,2,3,3a,4,5,6,6a-octahydroimidazo[4.5-d]imidazole Following the procedure of Example 1, 3,3'-dimethoxybenzil (1.0 g, 3.69 mmol) and 2-guanidinobenzimidazole (540 mg, 3.08 mmol) in methanol (40 mL) was treated with a solution of sodium hydroxide (200 mg, 5 mmol) in 5 mL of water. The title compound was isolated as pale yellow crystals (655 mg, 73% yield). mp: 276–278 ° C. (dec);MS (ESI) m/z 585 [M+H]+.

EXAMPLE 5

Preparation of 2,5-bis[2-benzimidazolylimino]-3a, 6a-bis(4-methylphenyl)-1,2,3,3a4,5,6,6a-octahydroimidazo[4.5-d]imidazole Following the procedure of Example 1, 4,4'-dimethylbenzil (1.91 g, 12 mmol) and 2-guanidinobenzimidazole (2.10 g, 10 mmol) in methanol (60 mL) was treated with a solution sodium hydroxide (400 mg, 10 mmol) in 10 mL of water. The orange solid was filtered, dissolved 40 mL of 10% acetic acid and filtered. The filtrate was then neutralized with aqueous sodium hydroxide to yield the title compound precipitated as a pale yellow solid (185 mg, 7% yield). mp: 245–248 ° C. (dec); MS (ESI) m/z 553 [M+H]$^+$.

EXAMPLE 6

Preparation of 2,5-bis[2-benzimidazolylimino]-3a, 6a-bis(4-fluorophenyl)-1,2,3,3a,4,5,6,6a-octahydroimidazo[4,5-d]imidazole Following the procedure of Example 1, 4,4'-difluorobenzil (1.0 g, 4.06 mmol) and 2-guanidinobenzimidazole (0.6 g, 3.4 mmol) in methanol (40 mL) was treated with a solution of sodium hydroxide (200 mg, 5 mmol) in 5 mL of water. The title compound was isolated as pale yellow crystals (750 mg, 79% yield). MS (ESI) m/z 561 [M+H]+.

EXAMPLE 7

Preparation of 2,5-bis[2-benzimidazolylimino]-3a, 6a-bis(6-methyl-2-pyridyl)-1,2,3,3a,4,5,6,6a-octahydroimidazo[4,5-d]imidazole Following the procedure of Example 1, 6,6'-dimethyl-2, 2'-pyridil (100 mg, 0.41 mmol) and 2-guanidinobenzimidazole (60 mg, 0.35 mmol) in methanol (5 mL) was treated with a solution of sodium hydroxide (20 mg, 0.55 mmol) in 0.5 mL of water. The title compound was isolated as pale yellow crystals (55 mg, 28% yield). MS (ESI) m/z 555 [M+H]+.

EXAMPLE 8

Preparation of 2,5-bis[2-benzimidazolylimino]-3a-(2-pyridyl)-6a-phenyl-1,2,3,3a,4,5,6,6a-octahydroimidazo[4,5-d]imidazole Following the procedure of Example 1, 1 -phenyl-2-(2-pyridinyl)ethanedione (800 mg, 3.79 mmol) and 2-guanidinobenzimidazole (560 mg, 3.15 mmol) in methanol (20 mL) was treated with a solution of sodium hydroxide (40 mg, 1.0 mmol) in 1 mL of water. The title compound was isolated as pale yellow crystals (160 mg, 20% yield). $^1$H NMR (300 z, d$_6$-DMSO) δ 12.0 (br. s, NH, 1H) 11.5 (br s, NH, 2 H), 10.0 (br s, NH, I H), 8.6 br s, NH, 1 H), 8A1 (m, 2 H), 7.55 (t, J=6.9 Hz, 2 H), 7.30–7.10 (m, 8 H), 6.98 (dd, J=6.0, 3.1 Hz, 4 H); MS (ESI) m/z 526 [M+H+.

EXAMPLE 9

Preparation of 2,5-bis[2-benzimidazolylimino]-3a-(4-pyridyl)-6a-phenyl-1,2,3,3a,4,5,6,6a-octahydroimidazo[4,5-d]imidazole Following the procedure of Example 1, 1 -phenyl-2-(4-pyridinyl)ethanedione (500 mg, 2.42 mmol) and 2-guanidinobenzimidazole (1.0 g, 6.0 mmol) in methanol (10 mL) was treated with a solution of sodium hydroxide (40 mg, 1.0 mmol) in 1 mL of water. The title compound was isolated as pale yellow crystals (45 mg, 3% yield). $^1$H NMR (300 MHz, d$_6$-DMSO) δ 11.5 (br s, NH, 1 H), 1 1.0 (br.s, NH, 1H), 10.0 (br s, NH, 1 H), 8.6 (br s, NH, 1 H), 8.4 (m, 2 H), 7.4–6.8 (m, 15H); MS (ESI) m/z 526 [M+H]+.

EXAMPLE 10

Preparation of 2,5-bis[(5-methyl-2-benzimidazolyl) imino]-3a,6a-bis(2-pyridyl)1,2,3,3a,4,5,6,6a-octahydroimidazo[4,5-d]imidazole Following the procedure of Example 1, 2,2'-pyridil (603 mg, 2.84 mmol) and 5-methyl-2-guanidinobenzimidazole (489 mg, 2.58 mmol) in methanol (17 mL) was treated with a solution of sodium hydroxide (113.6 mg, 2.84 mmol) in 2.8 mL of water. The title compound was isolated as a grey powder (450 mg, 63% yield). mp: 290–291 ° C. (dec); $^1$H NMR (300 MHz, d$_6$-DMSO) δ 11.3 br s, NH, 2 H), 10.0 (br s, NH, 2 H), 8.5 (br s, NH, 2 H), 8.32 (d, J=4.2 Hz, 2 H), 7.54 (t, J=7.6 Hz, 2 H), 7.31 (d, J=7.6 Hz, 2 H), 7.16 (d, J=7.8 Hz, 2 H), 7.16–7.09 (m, 2 H), 7.09 (s, 2 H), 7.14 br s, 2 H), 6.86 (d, J=7.8, Hz, 2 H), 2.34 (s, 6 H); MS (ESI) m/z 555 [M+H]+.

EXAMPLE 11

Preparation of 2,5-bis[(5-nitro-2-benzimidazolyl) imino]-3a,6a-bis(2-pyridyl)-1,2,3,3a,5,6,6a-octahydroimidazo[4,5-d]imidazole Following the procedure of Example 1, 2,2'-pyridil (245 mg, 1.15 mmol) and 5-nitro-2-guanidinobenzimidazole (254 mg, 1.15 mmol) in methanol (6.9 mL) was treated with a solution of sodium hydroxide (46 mg, 1.15 mmol) in 1.1 mL of water. The title compound was isolated as orange crystals (182 mg, 51%). mp: 340–350 ° C. (dec); MS (ESI) m/z 617 [M+H]+.

EXAMPLE 12

Preparation of 2,5-bis[(5-chloro-2-benzimidazolyl) imino]-3a,6a-bis(2-pyridyl-1,2,3,3a,4,5,6,6a-octahydroimidazo]4,5-d]imidazole Following the procedure of Example 1, 2,2'-pyridil (352 mg, 1.66 mmol) and 5-methyl-2-guanidinobenzimidazole (350 mg, 1.66 mmol) in methanol (10 mL) was treated with a solution of sodium hydroxide (66.4 mg, 1.66 mmol) in 2.5 mL of water. The title compound was isolated as a brownish solid (247 mg, 50%). MS (ESI) m/z 596 [M+H]+.

EXAMPLE 13

Preparation of 2,5-bis[(4-methyl-2-thiazolyl)imino]-3a,6a-bis(2-pyridyl)-1,2,3,3a,4,5,6a-octahydroimidazo[4,5-d]imidazole Following the procedure of Example 1, 2,2'-pyridil (1.06 g, 5.0 mmol) and 4-methylthiazol-2-ylguanidine hydrochloride (1.35 g, 7.0 mmol) in methanol (30 mL) was treated with a solution of sodium hydroxide (450 mg, 11.25 mmol) in 7.5 mL of water. The precipitate was filtered, dissolved 30 mL of 10% acetic acid and filtered; the filtrate was then neutralized with aqueous sodium hydroxide. The title compound precipitated as a tanned solid (265 mg, 16% yield). mp: >300 ° C. (dec); MS (ESI) m/z 489 [M+H]+.

EXAMPLE 14

Preparation of 2,5-bis[2-benzoxazolylimino]-3a,6a-bis(2-pyridyl)-1,2,3a,4,5,6,6a-octahydroimidazo[4,5-d]imidazole Following the procedure of Example 1, 2,2'-pyridil (301 mg, 1.42 mmol) and 2-guanidinobenzoxazole (250 mg, 1.42 mmol) in methanol (12 mL) was treated with a solution of sodium hydroxide (56.7 mg, 1.42 mmol) in 2 mL of water. The title compound was isolated as a brownish solid (151 mg, 40%). $^1$H NMR (300 MHz, d6-DMSO) δ 10.28 (s, NH, 4 H), 8.36 (d, J=4.6 Hz, 2 H), 7.57 (td, J=7.8 1.8 Hz, 2 H), 7.47 (d, J=7.8 Hz, 2 ),7.39 (d, J=7.8 Hz, 2 H), 7.30 (d, J=4.6 Hz, 2 H), 7.19 (dt, J=7.7, 1.3 Hz, 2 H), 7.16–7.10 (m, 4 H); MS (ESI) m/z 529 [M+H]+.

EXAMPLE 15

Preparation of 2,5-bis[(4-methyl-2-benzimidazolyl) imino]-3a6a-bis(2-pyridyl)-1,2,2a,4,5,6,6a-octahydroimidazo[4,5-d]imidazole Following the procedure of Example 1,2,2'-pyridil (1.87 g, 8.83 mmol) and 4-methyl-2-guanidinobenzimidazole (2.0 g, 10.5 mmol) in methanol (63 mL) was treated with a solution of sodium hydroxide (420 mg, 10.5 mmol) in 6 mL of water. The title compound was isolated as white crystals (1.9 g, 65%). MS (ESI) m/z 555 [M+H]+.

EXAMPLE 16

Preparation of 5-[2-benzimidazolylimino]-2-[(4-methyl-2-benzimidazolyl)imino]-3a,6a-bis(2-pyridyl)-1,2,2a,4,5,6,6a-octahydroimidazo[4,5-d] imidazole bis(trifluoroacetate) salt A mixture of 2,2'-pyridil (135 mg, 0.636 mmol), 2-guanidinobenzimidazole (92.8 mg, 0.530 mmol) and 4-methyl-2-guanidinobenzimidazole (100 mg, 0.530 mmol) in methanol (3 mL) was treated with a solution of sodium hydroxide (38 mg, 0.95 mmol) in 0.5 mL of water and the resulting mixture was left standing at room temperature for 2 days. The crystalline material was filtered and purified by reversed phase preparative HPLC (Rainin Dynamax, 5 μM C$_{18}$ column: 21.4 mm×25 cm, elution with gradient acetonitrile-water containing 0.1% trifluoroacetic acid) to yield the title compound as a white powder (100 mg, 25%). MS (ESI) m/z 541 [M+H]+.

EXAMPLE 17

Preparation of 5-(2-benzimidazolylimino)-2-[(5-methyl-2-benzimidazolyl)imino]-3a,6a-bis(2-pyridyl)-1,2,3,3a,4,5,6,6a-octahydroimidazo[4,5-d] imidazole bis(trifluoroacetate) salt Following the procedure of Example 16, except substituting 5-methyl-2-guanidinobenzimidazole for 4-methyl-2-guanidinobenzimidazole, the title compound was prepared (88 mg, 11%). $^1$H NMR (300 MHz, d$_6$-DMSO) δ 13.0 (br s, NH, 4 H), 9.8 (br s, NH, 4 H), 8.39 (d, J=4.3 Hz, 2 H), 7.64 (td, J=7.8, 1.7 Hz, 2 H), 7.57 (d, J=7.8 Hz, 2 H), 7.49–7.46 (m, 2 H), 7.38–7.33 (m, 3 H), 7.27 (s, 1 H), 7.21–7.13 (m, 3 H), 2.44 (s, 3 H); MS (ESI) m/z 541 [M+H]+.

EXAMPLE 18

Preparation of 2,5-bis[(1-methyl-2-benzimidazolyl) imino]-3a,6a-bis(2-pyridyl-1,2,3,3a,4,5,6,6a-octahydromidazo[4,5-d]imidazole bis (trifluoroacetate) salt Following the procedure of Example 1, 2,2'-pyridil (187 mg, 0.88 mmol) and 1-methyl-2-guanidinobenzimidazole (0.20 g, 1.57 mmol) in methanol (6 mL) was treated with a solution of sodium hydroxide (60 mg, 1.5 mmol) in 0.6 mL of water. The crystalline material was filtered and purified by reversed phase preparative HPLC (Rainin Dynamax, 5 μM C$_{18}$ column: 21.4 mm×25 cm, elution with gradient acetonitrile-water containing 0.1% trifluoroacetic acid) to yield the title compound as a white powder (200 mg, 48%). $^1$H NMR (300 MHz, d$_6$-DMSO) δ 9.9 (br s, NH, 4 H), 8.41 (d, J=4,5 Hz, 2 H), 7.68–7.62 (m, 4 H), 7.54 (d, J=7.7 Hz, 2 H), 7.55–7.50 (m, 2 H), 7.39–7.36 (m, 4 H), 7.20 (ddd, J=7.3,4.9, 1.0 Hz, 2 H), 3.78 (s, 6 H); MS (ESI) m/z 555 [M+H]+.

EXAMPLE 19

Preparation of 5-(2-benzimidazolylimino)-2-[(5-fluoro-2-benzimidazolyl)imino]-3a,6a-bis(2-pyridyl)-1,2,3,3a,4,5,6,6a-octahydroimidazo[4,5-d] imidazole bis(trifluoroacetate) salt A mixture of 2,2'-pyridil (345 mg, 1.6 mmol), 2-guanidinobenzimidazole (181 mg, 1.036 mmol) and 5-fluoro-2-guanidinobenzimidazole (250 mg, 1.036 mmol) in methanol (3 mL) was treated with a solution of sodium hydroxide (60 mg, 1.5 mmol) in 0.5 mL of water and the resulting mixture was left standing at room temperature for 2 days. The crystalline material was filtered and purified by reversed phase preparative HPLC (Rainin Dynamax, 5 μM C$_{18}$ column: 21.4 mm×25 cm, elution with gradient acetonitrile-water containing 0.1% trifluoroacetic acid) to yield the title compound as a white powder (92 mg, 12%); $^1$H NMR (300 MHz, d$_6$-DMSO) δ 13.2 (br s, NH, 2 H), 9.8 (br s, NH, 4 H), 8.40 (d, J=4.2 Hz, 2 H), 7.64 (td, J=7.6, 1.2 Hz, 2 H), 7.55 (d, J=7.5 Hz, 2 H), 7.49–7.43 (m, 3 H), 7.34–7.30 (m, 3 H), 7.19 (dd, J=7.0, 5.0 Hz, 2 H); MS (ESI) m/z 545 [M+H]+.

EXAMPLE 20

Preparation of 2,5-bis[(5-fluoro-2-benzimidazolyl) imino]-3a,6a-bis(2-pyridyl-1,2,3,3a4,5,6,6a-octahydroimidazo[4,5-d]imidazole bis (trifluoroacetate) salt A mixture of 2,2'-pyridil (262 mg, 1.2 mmol) and 5-fluoro-2-guanidinobenzimidazole (200 mg, 1.04 mmol) in methanol (3 mL) was treated with a solution of sodium hydroxide (60 mg, 1.5 mmol) in 0.6 +1mL of water. The crystalline material was filtered and purified by reversed phase preparative HPLC (Rainin Dynamax, 5 μM C$_{18}$ column: 21.4 mm×25 cm, elution with gradient acetonitrile-water containing 0.1% trifluoroacetic acid) to yield the title compound as a white powder (147 mg, 37%). $^1$H NMR (300 MHz, d$_6$-DMSO) δ 13.0 (br s, NH,2H),9.9(brs,NH,4H),8.39 (d,J=4.6 Hz,2H),7.64(td,J=7.7 1.6 Hz,2 H), 7.52 (d, J=7.8 Hz, 2 ), 7.45–7.41 (m, 2 H), 7.32–7.28 (m, 2 H), 7.21–7.16 (m, 2 H), 7.15–7.11 (m, 2 H); MS (ESI) m/z 563 [M+H]+.

EXAMPLE 21

Preparation of 5-(2-benzimidazolylimino)-2-[(1-methyl-2-benzimidazolyl)imino]-3a,6a-bis(2-pyridyl)-1,2,3,3a,4,5,6,6a-octahydroimidazo[4,5-d] imidazole bis(trifluoroacetate) salt A mixture of 2,2'-pyridil (265 mg, 1.25 mmol), 2-guanidinobenzimidazole (231 mg, 1.32 mmol) and 1-methyl-2-guanidinobenzimidazole (350 mg, 1.59 mmol) in methanol (3 mL) was treated with a solution of sodium hydroxide (95 mg, 2.4 mmol) in 0.5 mL of water and the resulting mixture was left standing at room temperature for 2 days. The crystalline material was filtered and purified by reversed phase preparative HPLC (Rainin Dynamax, 5 μM C$_{18}$ column: 21.4 mm×25 cm, elution with gradient acetonitrile-water containing 0.1% trifluoroacetic acid) to yield the title compound as a white powder (125 mg, 14%). $^1$H NMR (300 MHz, d$_6$-DMSO) δ 13.2 (br s, NH, 2 H), 9.9 (br s, NH, 4 H), 8.40 (d, J=4.3 Hz, 2 H), 7.68–7.62 (m, 3 H), 7.57 (d, J=7.8 Hz, 2 H), 7.50–7.47 (m, 3 H), 7.38–7.30 (m, 4 H), 7.20 (ddd, J=7.3, 5.3, 1.0 Hz, 2 H), , 3.78 (s, 3 H); MS (ESI) m/z 541 [M+H]+.

EXAMPLE 22

Preparation of 5-(2-benzimidazolylimino)-2-[(4-methyl-2-thiazolyl)imino]-3a,6a-bis(2-pyridyl)-1,2,2a,4,5,6,6a-octahydroimidazo[4,5-d]imidazole bis (trifluoroacetate) salt Following the procedure of Example 19 except substituting 4-methylthiazol-2-ylguanidine for 5-fluoro-2-guanidinobenzimidazole, the title compound was prepared (63 mg, 7%). MS (ESI) m/z 510 [M+H]+.

EXAMPLE 23

Preparation of 2,5-bis[(5-bromo-4-methyl-2-thiazolyl)imino]-3a,6a-bis(2-pyridyl)-1,2,3,3a,4,5,6a-octahydroimidazo[4,5-d]imidazole Following the procedure of Example 1, 2,2'-pyridil (215 mg, 1.016 mmol) and 5-bromo4-methyl-2-guanidinobenzimidazole (200 mg, 0.847 mmol) in methanol (3 mL) was treated with a solution of sodium hydroxide (51 mg, 1.27 mmol) in 0.5 mL of water. The title compound was isolated as white crystals (50 mg, 18%). MS (ESI) m/z 647 [M+H]+.

EXAMPLE 24

Preparation of 5-[2-benzimidazolylimino]-2-[(5-chloro-2-benzimidazolyl)imino]-3a,6a-bis(2-pyridyl)-1,2,2a,4,5,6,6a-octahydroimidazo[4,5-d] imidazole bis(trifluoroacetate) salt A mixture of 2,2'-pyridil (242 mg, 1.14 mmol), 2-guanidinobenzimidazole (166 mg, 0.95 mmol) and 5-chloro-2-guanidinobenzimidazole (200 mg, 0.95 mmol) in methanol (3 mL) was treated with a solution of sodium hydroxide (57 mg, 1.42 mmol) in 0.5 mL of water and the resulting mixture was left standing at room temperature for 2 days. The crystalline material was filtered and purified by reversed phase preparative HPLC (Rainin Dynamax, 5 μM C$_{18}$ column: 21.4 mm×25 cm, elution with gradient acetonitrile-water containing 0.1% trifluoroacetic acid) to yield the title compound as a white powder (173 mg, 23%). MS (ESI) m/z 562 [M+H]+.

EXAMPLE 25

Preparation of 2,5-bis[(5.6-dimethyl-2-benzimidazolyl)imino]-3a,6a-bis(2-pyridyl)-1,2,2a,4,5,6,6a-octahydroimidazo[4,5-d]imidazole bis (trifluoroacetate) salt A mixture of 2,2'-pyridil (254 mg, 1.2 mmol) and 5,6-dimethyl-2-guanidinobenzimidazole (203 mg, 1.0 mmol) in methanol (3 mL) was treated with a solution of sodium hydroxide (60 mg, 1.5 mmol) in 0.6 mL of water. The crystalline material was filtered and purified by reversed phase preparative HPLC (Rainin Dynamax, 5 μM C$_{18}$ column: 21.4 mm×25 cm, elution with gradient acetonitrile-water containing 0.1% trifluoroacetic acid) to yield the title compound as a white powder (170 mg, 42%). MS (ESI) m/z 583 [M+H]+.

EXAMPLE 26

Preparation of 5-[2-benzimidazolylimino]-2-[(5,6-dimethyl-2-benzimidazolyl)imino]-3a,6a-bis(2-pyridyl)-1,2,2a,4,5,6,6a-octahydroimidazo[4,5-d] imidazole bis(trifluoroacetate) salt A mixture of 2,2'-pyridil (254 mg, 1.2 mmol), 2-guanidinobenzimidazole (175 mg, 1.0 mmol) and 5,6-dimethyl-2-guanidinobenzimidazole (203 mg, 1.0 mmol) in methanol (3 mL) was treated with a solution of sodium hydroxide (60 mg, 1.5 mmol) in 0.5 mL of water and the resulting mixture was left standing at room temperature for 2 days. The crystalline material was filtered and purified by reversed phase preparative HPLC (Rainin Dynamax, 5 μM C$_{18}$ column: 21.4 mm×25 cm, elution with gradient acetonitrile-water containing 0.1% trifluoroacetic acid) to yield the title compound as a white powder (96 mg, 12%). $^1$H NMR (300 MHz, d6-DMSO) δ 13.1 (br s, NH, 2 H), 12.9 (br s, NH, 2 H), 9.9 (br s, NH, 2 H), 9.8 (br s, NH, 2 H), 8.39 (d, J=4.3 Hz, 2 H), 7.64 (td, J=7.9, 1.5 Hz, 2 H), 7.58 (d, J=7.9 Hz, 2 H), 7.48 (dd, J=6.0, 3.2 Hz, 2 H), 7.34–7.31 (m, 2 H), 7.25 (s, 2 H), 7.19 (dd, J=7.0,5.0 Hz, 2 H), 2.33 (s, 6 H); MS (ESI) m/z 555 [M+H]+.

EXAMPLE 27

Preparation of 2,5-bis[(5-carboxy-2-benzimidazolyl) imino]-3a,6a-bis(2pyridyl)-1,2,2a,4,5,6,6a-octahydroimidazo[4,5-d]imidazole bis trIfluoroacetate) salt Following the procedure of Example 25 except substituting 4-carboxy-2-guanidinobenzimidazole for 5,6-dimethyl-2-guanidinobenzimidazole, the title compound was prepared after purification by reversed phase preparative HPLC (42 mg, 10%). MS (ESI) m/z 615 [M+H]+.

EXAMPLE 28

Preparation of 5-[2-benzimidazolylimino]-2-[2-benzoxazolylimino]-3a,6a-bis(2-pyridl)-1,2,3a,4,5,6,6a-octahydroimidazo[4,5-d]imidazole bis (trifluoroacetate)

A mixture of 2,2'-pyridil (143 mg, 0.68 mmol), 2-guanidinobenzimidazole (100 mg, 0.56 mmol) and 2-guanidinobenzoxazole (100 mg, 0.56 mmol) in methanol (3 mL) was treated with a solution of sodium hydroxide (34 mg, 0.85 mmol) in 0.5 mL of water and the resulting mixture was left standing at room temperature for 2 days. The crystalline material was filtered and purified by reversed phase preparative HPLC (Rainin Dynamax, 5 μM C$_{18}$ column: 21.4 mm×25 cm, elution with gradient acetonitrile-water containing 0.1% trifluoroacetic acid) to yield the title compound as a white powder (42 mg, 10%). MS (ESI) m/z 528 [M+H]+.

EXAMPLE 29

Preparation of 2,5-bis[2-benzothiazolylimino]-3a, 6a-bis(2-pyridyl)-1,2,3a,4,5,6,6a-octahydroimidazo [4,5-d]imidazole A mixture of 2,2'-pyridil (212 mg, 1.0 mmol) and 2-guanidinobenzothiazole (403 mg, 2.2 mmol) in methanol (10 mL) was treated with a solution of sodium hydroxide (30 mg, 0.75 mmol) in 0.3 mL of water. The title compound was obtained as crystalline powder (407 mg, 73%). $^1$H NMR (300 MHz, d6-DMSO) δ 10.3 (br s, NH, 2 H), 8.38 (d, J=4.0 Hz, 2 H), 7.94 (s, J=7.8, 2H), 7.64 (m, 4 H), 7.41 (m, 4 H), 7.30 (t, J=7.5 Hz, 2 H), 7.18 (dd, J=7.5, 4.9 Hz, 2 H); MS (ESI) m/z 561 [M+H]+.

EXAMPLE 30

Preparation of 5-[2-benzimidazolylimino]-2-[2-benzothiazolylimino]-3a,6a-bis(2-pyridyl)-1,2,3a,4, 5,6,6a-octahydroimidazo[4,5-d]imidazole bis (trifluoroacetate)

A mixture of 2,2'-pyridil (255 mg, 1.2 mmol), 2-guanidinobenzimidazole (175.2 mg, 1.0 mmol) and 2-guanidinobenzothiazole (192 mg, 1.0 mmol) in methanol (10 mL) was treated with a solution of sodium hydroxide (40 mg, 1.0 mmol) in 0.4 mL of water and the resulting mixture was left standing at room temperature for 2 days. The crystalline material was filtered and purified by reversed phase preparative HPLC (Rainin Dynamax, 5 μM $C_{18}$ column: 21.4 mm×25 cm, elution with gradient acetonitrile-water containing 0.1% trifluoroacetic acid) to yield the title compound as a white powder (30 mg, 4%). $^1$H NMR (300 MHz, $d_6$-DMSO) δ 13.0 (br s, NH, 2 H), 9.8 (br s, NH, 2 H), 8.40 (d, J=4.0 Hz, 2 H), 7.83 (d, J=7.7, H), 7.55 (t, J=7.8 Hz, 2 H), 7.54 (d, J=7.7 Hz, 1 H), 7.50–7.38 (m, 4 H), 7.38–7.25 (m, 3 H), 7.23–7.15 (m, H); MS (ESI) m/z 544 [M+H]+.

EXAMPLE 31

Preparation of 5-[(2-benzimidazolylimino]1-2-[(5-carboxy-2-benzimidazolyl)imino]-3a,6a-bis(2-pyridyl)-1,2,3,3a,4,5,6,6a-octahydroimidazo[4,5-d] imidazole bis(trifluoroacetate) salt A mixture of 2,2'-pyridil (508 mg, 2.4 mmol), 2-guanidinobenzimidazole (350 mg, 2.0 mmol) and 5-carboxy-2-guanidinobenzimidazole (428 mg, 2.0 mmol) in methanol (6 mL) was treated with a solution of sodium hydroxide (120 mg, 3.0 mmol) in 0.8 mL of water and the resulting mixture was left standing at room temperature for 2 days. A total of 490 mg of a crystalline material was obtained, a portion of which (250 mg) was purified by reversed phase preparative HPLC (Rainin Dynamax, 5 μM $C_{18}$ column: 21.4 mm×25 cm, elution with gradient acetonitrile-water containing 0.1% trifluoroacetic acid) to yield the title compound as a white powder (50 mg, 6%).MS (ESI) m/z 571 [M+H]+.

EXAMPLE 32

Preparation of 2,5-bis[(5-iodo-2-benzimidazolyl) imino]-3a,6a-bis(2-pyridyl)-1,2,3,3a,4,5,6,6a-octahydroimidazo[4,5-d]imidazole bis (trifluoroacetate) salt and 5-[2-benzimidazolylimino]-2-[(5-iodo-2-benzimidazolyl) imino]-3a,6a-bis(2-pyridyl)-1,2,2a,4,5,6,6a-octahydroimidazo[4,5-d]imidazole bis (trifluoroacetate) salt A solution of 2,5-bis[2-benzimidazolylimino]-3a,6a-bis (2-pyridyl)-1,2,3,3a,4,5,6,6a-octahydroimidazo[4,5-d] imidazole (2.0 g, 3.8 mmol) in a mixture of 35 mL of N,N-dimethyl formamide, 3.5 mL of acetic acid and 3.5 mL was treated with N-iodosuccinimide (1.71 g, 7.6 mmol) and the resulting mixture was stirred for 3 d at room temperature. The solvent was evaporated and the residue partitioned between ethyl acetate and water; the aqueous layer was neutralized with sodium bicarbonate solution and extracted with ethyl acetate twice. The combined organic extracts were washed with water, brine and dried over anhydrous sodium sulfate. The solvent was evaporated under reduced pressure to yield a solid material (3.2 g); a portion of it (1.0 g) was purified by reversed phase preparative HPLC (Rainin Dynamax, 5 μM $C_{18}$ column: 21.4 mm×25 cm, elution with gradient acetonitrile-water containing 0.1% trifluoroacetic acid) to yield the title compounds as white powders. 5-iodo derivative (12.5 mg, 1%): $^1$H NMR (300 MHz, d6-DMSO) δ 13.0 (brs,NH,2H), 10.0(brs,NH,2H), 8.39(d,J=4.7 Hz,2H), 7.64(t,J=5.9 Hz,2 H), 7.40–7.60 (m, 4 H), 7.32 (m, 2 H), 6.98 (dd, J=4.6, 3.2 Hz, 2 H); MS (ESI) m/z 653 [M+H]+. 5,5'-diiodo derivative (62.5 mg, 12%): $^1$H NMR (300 MHz, $d_6$-DMSO) δ 9.9 (br s, NH, 2 H), 8.40 (d, J=4,5 Hz, 2 H), 7.74 (s, 2 H),7.62 (t, J=5.9, 1.7 Hz, 2 H), 7.45–7.56 (m, 4 H), 7.28 (d, 2 H), 7.19 (m, 3 H); MS (ESI) m/z 779 [M+H]+.

EXAMPLE 33

Preparation of 2,5-bis[2-benzimidazolylimino]-3a, 6a-bis(4-bromophenyl)-1,2,3,3a,4,5,6,6a-octahydroimidazo[4,5-d]imidazole Following the procedure of Example 1, 4,4'-dibromobenzil (4.42 g, 12 mmol) and 2-guanidinobenzimidazole (1.75 g, 10 mmol) in methanol (100 mL) was treated with a solution of sodium hydroxide (400 mg, 10 mmol) in 10 mL of water. The title compound was isolated as pale yellow crystals (800 mg, 24% yield). mp: 274–278 ° C. (dec); MS (ESI) m/z 683 [M+H]$^+$.

EXAMPLE 34

Preparation of 2,5-bis[2-benzimidazolylimino]-3a, 6a-bis(4-trifluoromethylphenyl)-1,2,3,3a,4,5,6,6a-octahydroimidazo[4,5-d]imidazole Following the procedure of Example 1, 4,4'-trifluoromethylbenzil (0.253 g, 0.73 mmol) and 2-guanidinobenzimidazole (0.154 g, 0.88 mmol) in methanol (10 mL) was treated with a solution of sodium hydroxide (35.2 mg, 0.88 mmol) in 1 mL of water. The title compound was isolated as pale yellow crystals (180 mg, 62% yield). MS (ESI) m/z 661 [M+H]$^+$.

EXAMPLE 35

Preparation of 2,5-bis[2-benzimidazolylimino]-3a-(3-chlorophenyl)-6a-phenyl-1,2,3,3a,4,5,6,6a-octahydroimidazo[4,5-d]imidazole Following the procedure of Example 1, 1-(3-chlorophenyl)-2-phenylethanedione (0.25 g, 1.0 mmol) and 2-guanidinobenzimidazole (0.215 g, 1.2 mmol) in methanol (12 mL) was treated with a solution of sodium hydroxide (48 mg, 1.2 mmol) in 1.2 mL of water. The title compound was isolated as pale yellow crystals (130 mg, 39% yield). MS (ESI) m/z 559 [M+H]$^+$.

EXAMPLE 36

Preparation of 2,5-bis[2-benzimidazolylimino]-3a-(2-chlorophenyl)-6a-phenyl-1,2,3,3a,4,5,6,6a-octahydroimidazo[4,5-d]imidazole Following the procedure of Example 1, 1-(2-chlorophenyl)-2-phenylethanedione (0.25 g, 1.0 mmol) and 2-guanidinobenzimidazole (0.215 g, 1.2 mmol) in methanol (12 mL) was treated with a solution of sodium hydroxide (48 mg, 1.2 mmol) in 1.2 mL of water. The title compound was isolated as pale yellow crystals (130 mg, 39% yield). MS (ESI) m/z 559 [M+H]$^+$.

EXAMPLE 37

Preparation of 5-(2-benzimidazolylimino)-2-[(5-methyl-2-benzimidazolyl)imino]-3a-(2-pyridyl)-6a-phenyl-1,2,3,3a,4,5,6,6a-octahydroimidazo[4,5-d] imidazole bis(trifluoroacetate) salt A mixture of 2-phenyl-1-(2-pyridyl)ethanedione (253 mg, 1.2 mmol), 2-guanidinobenzimidazole (175 mg, 1.0 mmol) and 5-methyl-2-guanidinobenzimidazole (189 mg, 1.0 mmol) in methanol (6 mL) was treated with a solution of sodium hydroxide (40 mg, 0.95 mmol) in 1.0 mL of water and the resulting mixture was left standing at room temperature for 2 days. The crystalline material was filtered and purified by reversed phase preparative HPLC (Rainin Dynamax, 5 mM $C_{18}$ column: 21.4 mm×25 cm, elution with gradient acetonitrile-water containing 0.1% trifluoroacetic acid) to yield the title compound as a white powder (20 mg, 5%). MS (ESI) m/z 540 [M+H]$^+$.

EXAMPLE 38

Preparation of 2,5-bis[(1 -methyl-2-benzimidazolyl) imino]-3a,6a-diphenyl-1,2,3,3a,4,5,6,6a-octahydromidazo[4,5-d]imidazole A solution of benzil (210 mg, 1.0 mmol) and 1-methyl-2-guanidinobenzimidazole (207 g, 1.1 mmol) in ethanol (5 mL) was treated with sodium hydroxide (40 mg, 1.0 mmol) in 0.8 mL of water and the resulting mixture was refluxed for 2 hours. The title compound precipitated and was isolated as a light yellow powder (125 mg, 41% yield). MS (ESI) m/z 553 [M+H]$^+$.

EXAMPLE 39

Preparation of 2,5-bis[(1-methyl-2-benzimidazolyl) imino]-3a,6a-bis(4-methylphenyl)-1,2,3,3a,4,5,6,6a-octahydromidazo[4,5-d]imidazole A solution of 4,4'-dimethylbenzil (238 mg, 1.0 mmol) and 1-methyl-2-guanidinobenzimidazole (207 g, 1.1 mmol) in ethanol (5 mL) was treated with sodium hydroxide (40 mg, 1.0 mmol) in 0.8 mL of water and the resulting mixture was refluxed for 2 hours. The title compound precipitated and was isolated as a yellow powder (50 mg, 16% yield). MS (ESI) m/z 581 [M+H]$^+$.

EXAMPLE 40

Preparation of 2,5-bis[(1-methyl-2-benzimidazolyl) imino]-3a,6a-bis(4-bromophenyl)-1,2,3,3a,4,5,6,6a-octahydromidazo[4,5-d]imidazole A solution of 4,4'-dibromobenzil (368 mg, 1.0 mmol) and 1-methyl-2-guanidinobenzimidazole (207 g, 1.1 mmol) in ethanol (5 mL) was treated with sodium hydroxide (40 mg, 1.0 mmol) in 0.8 mL of water and the resulting mixture was refluxed for 2 hours. The title compound precipitated and was isolated as a pale yellow powder (320 mg, 82% yield). MS (ESI) m/z 711 [M+H]+.

EXAMPLE 41

Capsule Composition

An oral dosage form for administering a presently invented agonist of the G-CSF receptor is produced by filing a standard two piece hard gelatin capsule with the ingredients in the proportions shown in Table I, below.

TABLE I

| INGREDIENTS | AMOUNTS |
| --- | --- |
| 2,5-Bis[2-benzimidazolylimino]-3a,6a-bis(2-pyridyl)-1,2,3,3a,4,5,6,6a-octahydroimidazo[4,5-d]imidazole (Compound 1) | 25 mg |
| Lactose | 55 mg |
| Talc | 16 mg |
| Magnesium Stearate | 4 mg |

EXAMPLE 42

Injectable Parenteral Composition

An injectable form for administering a presently invented agonist of the G-CSF receptor is produced by stirring 1.5% by weight of 2,5-Bis[2-benzimidazolylimino]-3a,6a-diphenyl-1,2,3,3a,4,5,6,6a-octahydroimidazo[4,5-d] imidazole (Compound 2) in 10% by volume propylene glycol in water.

EXAMPLE 43

Tablet Composition

The sucrose, calcium sulfate dihydrate and a presently invented agonist of the G-CSF receptor, as shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
| --- | --- |
| 2,5-Bis[2-benzimidazolylimino]-3a,6a-bis(2-pyridyl)-1,2,3,3a,4,5,6,6a-octahydroimidazo[4,5-d]imidazole (Compound 1) | 20 mg |
| calcium sulfate dihydrate | 30 mg |
| sucrose | 4 mg |
| starch | 2 mg |
| talc | 1 mg |
| stearic acid | 0.5 mg |

While the preferred embodiments of the invention are illustrated by the above, it is to be understood that the invention is not limited to the precise instructions herein disclosed and that the right to all modifications coming within the 10 scope of the following claims is reserved.

What is claimed is:

1. A compound of the Formula (1):

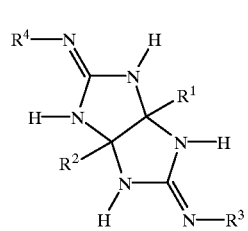

(I)

wherein $R^1$, $R^2$, $R^3$ and $R^4$ are independently aryl, where aryl is cyclic or polycyclic aromatic $C_3$–$C_{12}$, optionally containing one or more heteroatoms, provided that when C

23 is 3 the aromatic ring contains at least two heteroatoms, and when C is 4 the aromatic ring contains at least one heteroatom, and optionally substituted with one or more substituents selected from the group consisting of: C(O)NR$^6$R$^7$ and NR$^6$R$^7$, aryloxy, cycloalkyl, substituted cycloalkyl, alkyl, C$_6$–C$_{12}$aryl, alkoxy, acyloxy, substituted C$_6$–C$_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, C$_6$–C$_{12}$aryl, substituted C$_6$–C$_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where R$^6$ is hydrogen or alkyl, n is 0–2, R$^7$ is hydrogen or alkyl and R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl; or a pharmaceutically acceptable salt, hydrate, solvate or ester thereof.

2. A compound of claim 1 in which R$^1$ and R$^2$ are independently phenyl, furyl, thienyl or pyridyl all of which are unsubstituted or substituted with a substituent selected from the group consisting of: halogen, C$_{1-5}$alkyl, C$_{3-6}$cycloalkyl and —O—C$_{1-3}$alkyl;

R$^3$ and R$^4$ are independently pyridyl, benzimidazolyl, benzothiazolyl, benzoxazolyl, thiazolyl or imidazolyl all of which are unsubstituted or substituted with one or two substituents selected from the group consisting of: halogen, amino, cyano, N-acylamino, C$_{1-3}$ alkyl, —O—C$_{1-3}$ alkyl, nitro, —CO$_2$H and CF$_3$; or a pharmaceutically acceptable salt, hydrate, solvate or ester thereof.

3. The compound of claim 1 selected from:

2,5-bis[2-benzimidazolylimino]-3a,6a-bis(2-pyridyl)-1,2,3,3a,4,5,6,6a-octahydroimidazo[4,5-d] imidazole, 2,5-bis[2-benzimidazolylimino]-3a-(2-pyridyl)-6a-phenyl-1,2,3,3a,4,5,6,6a-octahydroimidazo[4,5-d]imidazole, 5-[2-benzimidazolylimino]-2-[(4-methyl-2-benzimidazolyl)imino]-3a,6a-bis(2-pyridyl)-1,2,2a,4,5,6,6a-octahydroimidazo[4,5-d]imidazole bis (trifluoroacetate) salt, 5-(2-benzimidazolylimino)-2-[(5-methyl-2-benzimidazolyl)imino]-3a,6a-bis(2-pyridyl)-1,2,3,3a,4,5,6,6a-octahydroimidazo[4,5-d]imidazole bis (trifluoroacetate) salt, 2,5-bis[(1-methyl-2-benzimidazolyl)imino]-3a,6a-bis(2-pyridyl)-1,2,3,3a,4,5,6,6a-octahydromidazo[4,5-d] imidazole bis(trifluoroacetate) salt, and 5-[2-benzimidazolylimino]-2-[(5,6-dimethyl-2-benzimidazolyl)imino]-3a,6a-bis(2-pyridyl)-1,2,2a,4,5,6,6a-octahydroimidazo[4,5-d]imidazole bis (trifluoroacetate) salt, or a pharmaceutically acceptable salt, hydrate or solvate thereof.

24

4. The compound of claim 1 selected from:

2,5-bis[2-benzimidazolylimino]-3a,6a-diphenyl-1,2,3,3a,4,5,6,6a-octahydroimidazo[4,5-d]imidazole, 2,5-bis[2-benzimidazolylimino]-3a,6a-bis(2-furyl)-1,2,3,3a,4,5,6,6a-bis(2-pyridyl)octahydroimidazo[4,5-d]imidazole, 2,5-bis[2-benzimidazolylimino]-3a,6a-bis(3-methoxyphenyl)-1,2,3,3a,4,5,6,6a-octahydroimidazo[4,5-d]imidazole, 2,5-bis[2-benzimidazolylimino]-3a,6a-bis(4-methylphenyl)-1,2,3,3a,4,5 ,6,6a-octahydroimidazo[4,5-d]imidazole, 2,5-bis[2-benzimidazolylimino]-3a,6a-bis(4-fluorophenyl)-1,2,3,3a,4,5 ,6,6a-octahydroimidazo[4,5-d]imidazole, 2,5-bis[2-benzimidazolylimino]-3a,6a-bis(6-methyl-2-pyridyl)-1,2,3,3a,4,5,6,6a-octahydroimidazo[4,5-d]imidazole, 2,5-bis[2-benzimidazolylimino]-3a-(4-pyridyl)-6a-phenyl-1,2,3,3a,4,5,6,6a-octahydroimidazo[4,5-d]imidazole, 2,5-bis[(5-methyl-2-benzimidazolyl)imino]-3a,6a-bis(2-pyridyl)-1,2,3,3a,4,5,6,6a-octahydroimidazo[4,5-d]imidazole, 2,5-bis[(5-nitro-2-benzimidazolyl)imino]-3a,6a-bis(2-pyridyl)-1,2,3,3a,4,5,6,6a-octahydroimidazo[4,5-d]imidazole, 2,5-bis[(5-chloro-2-benzimidazolyl)imino]-3a,6a-bis(2-pyridyl)-1,2,3,3a,4,5,6,6a-octahydroimidazo[4,5-d]imidazole, 2,5-bis[(4-methyl-2-thiazolyl)imino]-3a,6a-bis(2-pyridyl)-1,2,3,3a,4,5,6a-octahydroimidazo[4,5-d]imidazole, 2,5-bis[2-benzoxazolylimino]-3a,6a-bis(2-pyridyl)-1,2,3a,4,5,6,6a-octahydroimidazo[4,5-d]imidazole, 2,5-bis[(4-methyl-2-benzimidazolyl)imino]-3a,6a-bis(2-pyridyl)-1,2,2a,4,5,6,6a-octahydroimidazo[4,5-d]imidazole, 5-(2-benzimidazolylimino)-2-[(5-fluoro-2-benzimidazolyl)imino]-3a,6a-bis(2-pyridyl)-1,2,3,3a,4,5,6,6a-octahydroimidazo[4,5-d]imidazole bis (trifluoroacetate) salt, 2,5-bis[(5-fluoro-2-benzimidazolyl)imino]-3a,6a-bis(2-pyridyl)-1,2,3,3a,4,5,6,6a-octahydroimidazo[4,5-d]imidazole bis(trifluoroacetate) salt, 5-(2-benzimidazolylimino)-2-[(1 -methyl-2-benzimidazolyl)imino]-3a,6a-bis(2-pyridyl)-1,2,3,3a,4,5,6,6a-octahydroimidazo[4,5-d]imidazole bis (trifluoroacetate) salt, 5-[2-benzimidazolylimino]-2-[(4-methyl-2-thiazolyl)imino]-3a,6a-bis(2-pyridyl)-1,2,2a,4,5,6,6a-octahydroimidazo[4,5-d]imidazole bis(trifluoroacetate) salt, 2,5-bis [(5-bromo-4-methyl-2-thiazolyl)imino]-3a,6a-bis(2-pyridyl)-1 ,2,3,3a,4,5,6a-octahydroimidazo[4,5-d] imidazole, 5-[2-benzimidazolylimino]-2-[(5-chloro-2-benzimidazolyl)imino]-3a,6a-bis(2-pyridyl)-1,2,2a,4,5,6,6a-octahydroimidazo[4,5-d]imidazole bis (trifluoroacetate) salt, 2,5-bis[(5,6-dimethyl-2-benzimidazolyl)imino]-3a;6a-bis(2-pyridyl)-1,2,2a,4,5,6,6a-octahydroimidazo[4,5-d] imidazole bis(trifluoroacetate) salt, 2,5-bis [(5-carboxy-2-benzimidazolyl)imino]-3a,6a-bis (2-pyridyl)-1,2,2a,4,5,6,6a-octahydroimidazo[4,5-d] imidazole bis(trifluoroacetate) salt, 5-[2-benzimidazolylimino]-2-[2-benzoxazolylimino]-3a, 6a-bis(2-pyridyl)-1,2,3a,4,5,6,6a-octahydroimidazo[4, 5-d]imidazole bis(trifluoroacetate) salt, 2,5-bis[2-benzothiazolylimino]-3a,6a-bis(2-pyridyl)-1 ,2,3a,4,5,6,6a-octahydroimidazo[4,5-d]imidazole, 5-[2-benzimidazolylimino]-2-[2-benzothiazolyl1no]-3a, 6a-bis(2-pyridyl)-1,2,3a,4,5,6,6a-octahydroimidazo[4, 5-d]imidazole bis(trifluoroacetate) salt, 5-[(2-benzimidazolylimino)]-2-[(5-carboxy-2-benzimidazolyl)imino]-3a,6a-bis(2-pyridyl)-1,2,3 ,3a, 4,5 ,6,6a-octahydroimidazo[4,5-d]imidazole bis (trifluoroacetate) salt, 2,5-bis [(5-iodo-2-benzimidazolyl)imino]-3a,6a-bis(2-pyridyl)-1,2,3,3a,4,5,6,6a-octahydroimidazo[4,5-d] imidazole bis(trifluoroacetate) salt, and 5-[2-benzimidazolylimino]-2-[(5-iodo-2-benzimidazolyl) imino]-3a,6a-bis(2-pyridyl)-1,2,2a,4,5,6,6a-octahydroimidazo[4,5-d]imidazole bis(trifluoroacetate) salt, or a pharmaceutically acceptable salt, hydrate or solvate thereof.

5. The compound of claim 1 selected from:

2,5-bis[2-benzimidazolylimino]-3a,6a-bis(4-bromophenyl)-1,2,3,3a,4,5,6,6a-octahydroimidazo[4, 5-d]imidazole, 2,5-bis[2-benzimidazolylimino]-3a,6a-bis(4-trifluoromethylphenyl)-1,2,3,3a,4,5,6,6a-octahydroimidazo[4,5-d]imidazole, 2,5-bis[2-benzimidazolylimino]-3a-(3-chlorophenyl)-6a-phenyl-1,2,3,3a,4,5,6,6a-octahydroimidazo[4,5-d] imidazole, 2,5-bis[2-benzimidazolylimino]-3a-(2-chlorophenyl)-6a-phenyl-1 ,2,3,3a,4,5,6,6a-octahydroimidazo[4,5-d] imidazole, 5-(2-benzimidazolylimino)-2-[(5-methyl-2-benzimidazolyl)imino]-6a-phenyl-3a-(2-pyridyl)-1,2, 3,3a,4,5,6,6a-octahydroimidazo[4,5-d]imidazole bis (trifluoroacetate) salt, 2,5-bis [(1 -methyl-2-benzimidazolyl)imino]-3a,6a-diphenyl-1,2,3,3a,4,5,6,6a-octahydromidazo[4,5-d] imidazole, 2,5-bis[(1 -methyl-2-benzimidazolyl)imino]-3a,6a-bis(4-methylphenyl)-1,2,3,3a,4,5,6,6a-octahydromidazo[4,5-d]imidazole, and 2,5-bis[(1 -methyl-2-benzimidazolyl)imino]-3a,6a-bis(4-bromophenyl)-1,2,3,3a,4,5,6,6a-octahydromidazo[4,5-d]imidazole.

6. A pharmaceutical composition comprising a pharmaceutically acceptable carrier and a compound of claim 1.

7. A method of enhancing leukocyte production in a subject which comprises administering to the subject a therapeutically effective amount of a compound of claim 2.

8. A method of treating neutropenia in a subject which comprises administering to the subject a therapeutically effective amount of a compound of claim 1.

9. A method of activating the G-CSF receptor in a subject which comprises administering to the subject a therapeutically effective amount of a compound of claim 1.

10. A method of treating bacterial infections which comprises administering to the subject a therapeutically effective amount of a compound of claim 1.

11. A method of treating fungal infections which comprises administering to the subject a therapeutically effective amount of a compound of claim 1.

12. A process for the preparation of a compound of Formula (I)

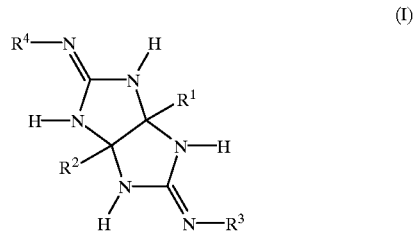

(I)

wherein $R^1$, $R^2$, $R^3$ and $R^4$ are as described in claim 1 which comprises:

reacting a 1,2-diketone of Formula (2)

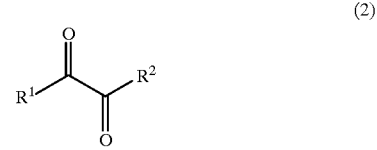

(2)

wherein $R^1$ and $R^2$ are as described in claim 1 with one or more guanidine derivatives of Formula (3)

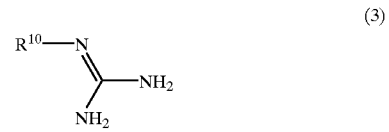

(3)

wherein $R^{10}$ is $R^3$ or $R^4$, such that when more than one guanidine derivative of Formula (3) is utilized $R^{10}$ does not have to be the same substituent, in a refluxing solvent with azeotropic removal of water, and thereafter optionally forming a pharmaceutically acceptable salt, hydrate or solvate thereof.

13. A process for the preparation of a compound of Formula (I)

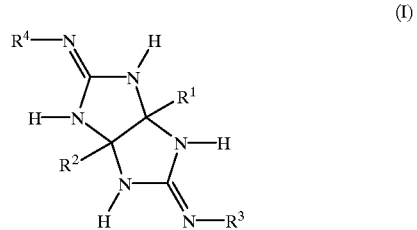

(I)

wherein $R^1$, $R^2$, $R^3$ and $R^4$ are as described in claim 1 which comprises:

reacting a 1,2-diketone of Formula (2)

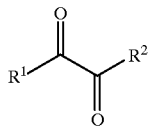

(2)

wherein $R^1$ and $R^2$ are as described in claim 1 with one or more guanidine derivatives of Formula (3

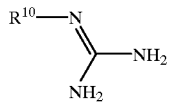

(3)

wherein $R^{10}$ is $R^3$ or $R^4$, such that when more than one guanidine derivative of Formula (3) is utilized $R^{10}$ does not have to be the same substituent, the presence of a base catalyst in a suitable protic solvent, and thereafter optionally forming a pharmaceutically acceptable salt, hydrate or solvate thereof.

14. A process for preparing a pharmaceutical composition containing a pharmaceutically acceptable carrier or diluent and an effective amount of a compound of the Formula (I) as described in claim 1 and pharmaceutically acceptable salts, hydrates, solvates and esters thereof which process comprises bringing the compound of the Formula (I) into association with the pharmaceutically acceptable carrier or diluent.

* * * * *